US010555661B2

(12) United States Patent
Hashimoto (10) Patent No.: US 10,555,661 B2
(45) Date of Patent: Feb. 11, 2020

(54) ENDOSCOPE SYSTEM

(71) Applicant: OLYMPUS CORPORATION, Tokyo (JP)

(72) Inventor: Susumu Hashimoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/214,198

(22) Filed: Dec. 10, 2018

(65) Prior Publication Data

US 2019/0104920 A1    Apr. 11, 2019

Related U.S. Application Data

(63) Continuation of application No. PCT/JP2017/021804, filed on Jun. 13, 2017.

(30) Foreign Application Priority Data

Jun. 27, 2016    (JP) ................. 2016-126758

(51) Int. Cl.
*A61B 1/06*    (2006.01)
*A61B 1/00*    (2006.01)
(Continued)

(52) U.S. Cl.
CPC ........ *A61B 1/00009* (2013.01); *A61B 1/0002* (2013.01); *A61B 1/00006* (2013.01);
(Continued)

(58) Field of Classification Search
None
See application file for complete search history.

(56) References Cited

U.S. PATENT DOCUMENTS

| 6,002,425 A | 12/1999 | Yamanaka et al. |
| 2002/0120179 A1 | 8/2002 | Abe |

(Continued)

FOREIGN PATENT DOCUMENTS

| JP | H10-085176 A | 4/1998 |
| JP | 2001-224555 A | 8/2001 |

(Continued)

OTHER PUBLICATIONS

International Search Report dated Aug. 22, 2017 issued in PCT/JP2017/021804.

*Primary Examiner* — Eileen M Adams
(74) *Attorney, Agent, or Firm* — Scully, Scott, Murphy & Presser, P.C.

(57) ABSTRACT

An endoscope system includes: a first processor configured to process a first imaging signal acquired by a first endoscope; a second processor communicably connected to the first processor and configured to process second imaging signal acquired by a second endoscope; a mode switch configured to switch a processing mode of image processing; an image processor configured to execute first image processing on the first imaging signal when the mode switch switches the processing mode to a first processing mode and to execute second image processing on an signal input from the second processor when the mode switch switches the processing mode to a second processing mode; and a video-signal output unit configured to generate a video signal for display based on an output signal from the image processor and output the video signal to an external device.

7 Claims, 5 Drawing Sheets

(51) Int. Cl.
*A61B 1/04* (2006.01)
*G06T 5/00* (2006.01)
*G06T 5/50* (2006.01)

(52) U.S. Cl.
CPC ...... *A61B 1/00011* (2013.01); *A61B 1/00105* (2013.01); *A61B 1/0005* (2013.01); *A61B 1/00124* (2013.01); *A61B 1/04* (2013.01); *A61B 1/06* (2013.01); *G06T 5/001* (2013.01); *G06T 5/50* (2013.01); *G06T 2207/10024* (2013.01)

(56) References Cited

U.S. PATENT DOCUMENTS

| | | | | |
|---|---|---|---|---|
| 2007/0273759 | A1* | 11/2007 | Krupnick | H04N 5/225 348/45 |
| 2009/0203965 | A1* | 8/2009 | Fujiyama | A61B 1/00096 600/130 |
| 2013/0146108 | A1* | 6/2013 | Suzuki | A61B 1/123 134/113 |
| 2017/0006271 | A1 | 1/2017 | Koizumi et al. | |

FOREIGN PATENT DOCUMENTS

| | | |
|---|---|---|
| JP | 2002-248077 A | 9/2002 |
| JP | 2004-236738 A | 8/2004 |
| JP | 2013-090750 A | 5/2013 |
| JP | 2014-113212 A | 6/2014 |
| JP | 2015-047459 A | 3/2015 |
| JP | 2016-096941 A | 5/2016 |
| WO | WO 2015/194421 A1 | 12/2015 |
| WO | WO 2017/047117 A1 | 3/2017 |
| WO | WO 2017/047321 A1 | 3/2017 |

\* cited by examiner

ENDOSCOPE SYSTEM

CROSS-REFERENCE TO RELATED APPLICATION

This application is a continuation of PCT International Application No. PCT/JP2017/021804 filed on Jun. 13, 2017 which claims the benefit of priority from Japanese Patent Application No. 2016-126758, filed on Jun. 27, 2016, the entire contents of which are incorporated herein by reference.

BACKGROUND

The present disclosure relates to an endoscope.

In medical fields, there are known endoscope systems that use an imaging device to capture an inside of a body of a subject and observe the inside of the body of the subject (for example, see Japanese Laid-open Patent Publication No. 2013-90750).

An endoscope system (electronic endoscope system) disclosed in Japanese Laid-open Patent Publication No. 2013-90750 includes: an endoscope (electronic endoscope) that is inserted into a body of a subject to capture an inside of the body of the subject and output imaging signals; a processor (processor device) that is connected to the endoscope in an attachable and detachable manner and performs predetermined image processing on imaging signals from the endoscope to generate video signals for display; and a display device (monitor) that is connected to the processor and presents images based on video signals from the processor. Then, a user such as a doctor observes the inside of the body of a subject with images presented on the display device.

SUMMARY

According to one aspect of the present disclosure, there is provided an endoscope system for being connected with processors configured to process imaging signals acquired by endoscopes that observe an inside of a subject, the endoscope system including: a first processor configured to process a first imaging signal acquired by a first endoscope; a second processor communicably connected to the first processor and configured to process second imaging signal acquired by a second endoscope; a mode switch provided in the first processor and configured to switch a processing mode of image processing to one of a first processing mode and a second processing mode in accordance with a connection state of the first processor and the first endoscope and a connection state of the second processor and the second endoscope; an image processor provided in the first processor and configured to execute first image processing on the first imaging signal when the mode switch switches the processing mode to the first processing mode and to execute second image processing on an signal input from the second processor when the mode switch switches the processing mode to the second processing mode; and a video-signal output unit configured to generate a video signal for display based on an output signal from the image processor and output the video signal to an external device.

The above and other features, advantages and technical and industrial significance of this disclosure will be better understood by reading the following detailed description of presently preferred embodiments of the disclosure, when considered in connection with the accompanying drawings.

DETAILED DESCRIPTION

With reference to the drawings, an aspect (hereafter, embodiment) for implementing the present disclosure is explained below. Here, the present disclosure is not limited to the embodiment described below. Furthermore, in description of the drawings, the same components are attached with the same reference numeral.

Schematic Configuration of Endoscope System

Figure 1:
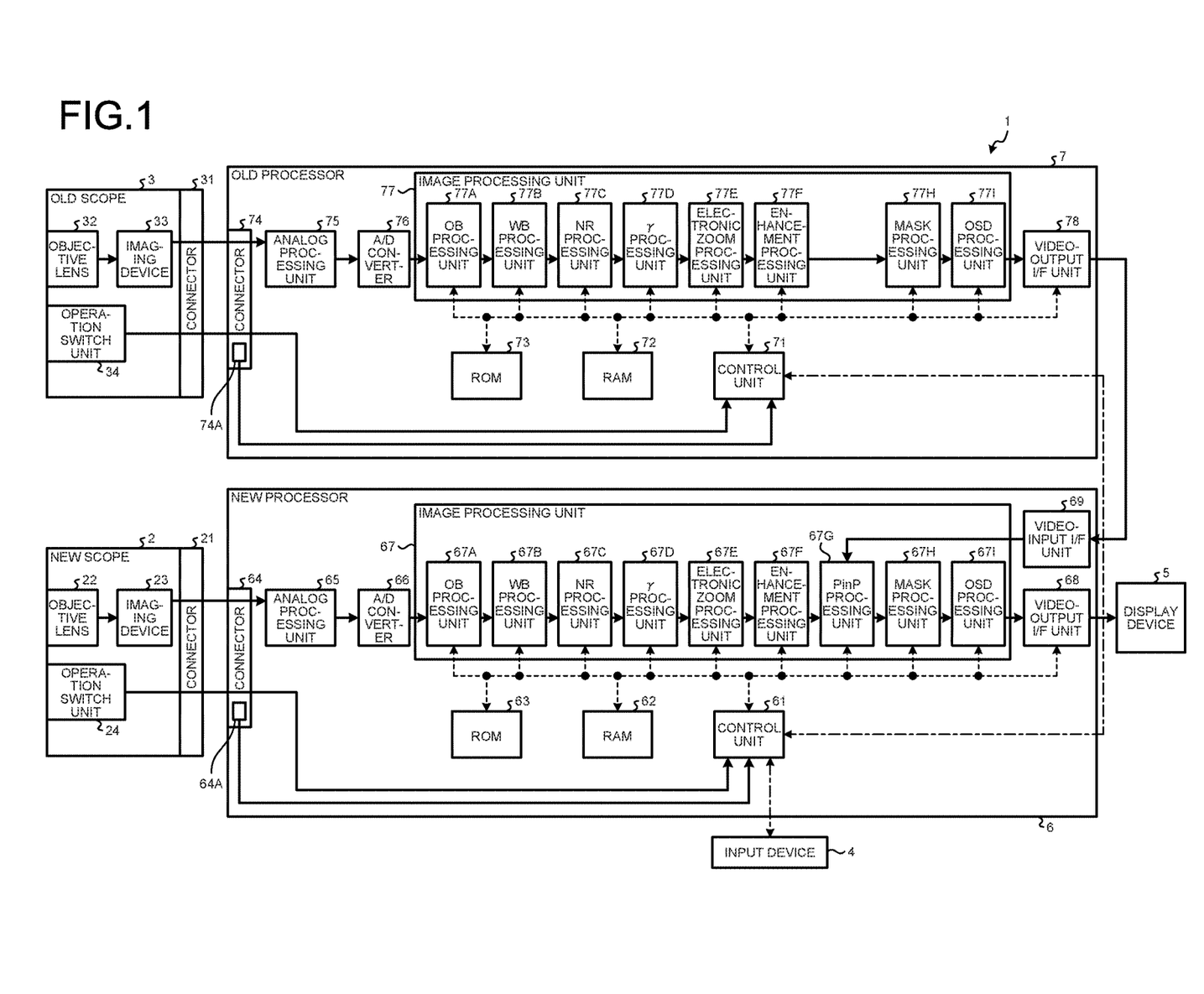
FIG. 1 is a block diagram that illustrates the configuration of an endoscope system according to an embodiment.

FIG. 1 is a block diagram that illustrates the configuration of an endoscope system 1 according to an embodiment.

The endoscope system 1 is a system used in medical fields to observe the inside (e.g., tracts such as large intestine) of a subject, such as person. As illustrated in FIG. 1, the endoscope system 1 includes two scopes, new and old scopes 2, 3, an input device 4, a display device 5, and two processors, new and old processors 6, 7.

Each of the two new and old scopes 2, 3 is inserted into the body of a subject to capture the inside of the body of the subject. Furthermore, any one of the two new and old scopes 2, 3 is used to observe the inside of the body of a subject by using the endoscope system 1.

The new scope 2 is a scope upgraded from the old scope 3, and it functions as a first endoscope. According to the present embodiment, the new scope 2 is configured as what is called a flexible endoscope that is soft and elongated in shape and that is inserted into the body of a subject. Furthermore, the new scope 2 is connected to only the new processor 6 through a connector 21 (FIG. 1) in an attachable and detachable manner. As illustrated in FIG. 1, the new scope 2 is provided with an objective lens 22 that focuses a subject image in the inside of the subject; an imaging device 23 that captures the subject image focused by the objective lens 22; and an operation switch unit 24 provided with various operation switches such as a release switch.

The old scope 3 functions as a second endoscope. According to the present embodiment, the old scope 3 is configured as a flexible endoscope in the same manner as the new scope 2. Furthermore, the old scope 3 is connected to only the old processor 7 through a connector 31 (FIG. 1) in an attachable and detachable manner. As illustrated in FIG. 1, the old scope 3 is provided with an objective lens 32, an imaging device 33, and an operation switch unit 34 in the same manner as the new scope 2.

Furthermore, the imaging devices 23, 33 are imaging sensors such as CCD (charge coupled device) or CMOS (complementary metal oxide semiconductor), which receive subject images focused by the objective lenses 22, 32 and convert them into electric signals. Then, each of the imaging devices 23, 33 outputs converted electric signals (analog signals). For example, the imaging device 23 is an imaging sensor having a large number of pixels as compared with the imaging device 33 due to a version upgrade from the old scope 3 to the new scope 2.

Hereafter, electric signals (analog signals) output from the imaging device 23 (the new scope 2) are first imaging signals, and electric signals (analog signals) output from the imaging device 33 (the old scope 3) are second imaging signals.

The input device 4 is configured by using a user interface, such as a keyboard or a mouse, and is connected to the new processor 6. Furthermore, the input device 4 receives user operation by the user, such as a doctor, and outputs information input due to the user operation to the new processor 6. That is, the input device 4 functions as an operation receiving unit.

The display device 5 is configured by using a presentation display that uses a liquid crystal, an organic EL (electro luminescence), or the like, and it is connected to the new processor 6. Furthermore, the display device 5 receives input of video signals for display from the new processor 6 and displays observation images, or the like, based on video signals for display.

The new processor 6 is a processor upgraded from the old processor 7, and it functions as a processor. The new processor 6 includes a control unit 61 (FIG. 1) such as a CPU (central processing unit), a RAM (random access memory) 62 (FIG. 1), a ROM (read only memory) 63 (FIG. 1), and the like, and it controls operation of the new and old scopes 2, 3, the display device 5, and the old processor 7 in an integrated manner in accordance with programs (including control programs) stored in the ROM 63.

The old processor 7 functions as an external processor. The old processor 7 has substantially the same configuration as that of the new processor 6, and it performs predetermined processing under the control of the new processor 6.

The detailed configurations of the new processor 6 and the old processor 7 are explained below.

Configuration of the New Processor

The new processor 6 is connectable to only the new scope 2 out of the new and old scopes 2, 3 through a connector 64. As illustrated in FIG. 1, the new processor 6 includes an analog processing unit 65, an A/D converter 66, an image processing unit (an image processor) 67, a video-output I/F unit 68, and a video-input I/F unit 69 in addition to the control unit 61, the RAM 62, and the ROM 63.

The analog processing unit 65 receives input of the first imaging signal (analog signal) from the new scope 2 and conducts analog processing, such as clamp processing or noise removal processing (CDS: correlated double sampling) on the first imaging signal.

The A/D converter 66 conducts A/D conversion on the first imaging signal (analog signal) on which analog processing has been conducted, and it outputs the converted first imaging signal (digital signal).

Here, as illustrated in FIG. 1, the connector 64 is provided with a connection detecting unit 64A that detects whether the new scope 2 is connected and outputs the signal that corresponds to a detection result to the control unit 61. Furthermore, in the old processor 7, similarly, a connector 74 (FIG. 1) to which the old scope 3 is connected is provided with a connection detecting unit 74A that detects whether the old scope 3 is connected and outputs the signal that corresponds to a detection result to a control unit 71.

Furthermore, the control unit 61 (the new processor 6) is communicatively connected to the control unit 71 (the old processor 7) through an undepicted connector, cable, or the like, and acquires a detection result of the connection detecting unit 74A through the communication. Then, in accordance with a detection result of each of the connection detecting units 64A, 74A, the control unit 61 switches the processing mode of the image processing unit 67 into any processing mode, a first processing mode (hereafter, referred to as a single mode) and a second processing mode (hereafter, referred to as a conventional-compatible mode).

Specifically, when the old scope 3 is not connected to the old processor 7 and the new scope 2 is connected to the new processor 6, the control unit 61 sets the single mode as the processing mode of the image processing unit 67. Conversely, when the new scope 2 is not connected to the new processor 6 and the old scope 3 is connected to the old processor 7, the control unit 61 sets the conventional-compatible mode as the processing mode of the image processing unit 67. That is, the control unit 61 functions as a mode switching unit (a mode switch).

The image processing unit 67 performs image processing, either first or second image processing, on input signals by using various parameters for image processing, stored in the ROM 63, under the control of the control unit 61. Specifically, when the single mode is set as the processing mode, the image processing unit 67 executes the first image processing on the first imaging signal (digital signal) output from the A/D converter 66. Furthermore, when the conventional-compatible mode is set as the processing mode, the image processing unit 67 executes the second image processing on external processing signals output from the old processor 7.

Here, the image processing unit 67 is capable of executing multiple types of image processing. In the example of the configuration illustrated in FIG. 1, the image processing unit 67 includes: an OB processing unit 67A that conducts optical black subtraction processing; a WB processing unit 67B that conducts white balance adjustment processing; an NR processing unit 67C that conducts noise reduction processing; a γ processing unit 67D that conducts gamma processing; an electronic zoom processing unit 67E that conducts electronic zoom processing; an enhancement processing unit 67F that conducts edge enhancement processing; a PinP processing unit 67G that conducts picture in picture processing; a mask processing unit 67H that conducts mask processing; and an OSD processing unit 67I that conducts on-screen display processing.

Furthermore, according to the present embodiment, all types of executable image processing (optical black subtraction processing, white balance adjustment processing, noise reduction processing, gamma processing, electronic zoom processing, edge enhancement processing, picture in picture processing, mask processing, and on-screen display processing in the example of FIG. 1) are set as the first image processing conducted on the first imaging signal (digital signal) in the single mode. Furthermore, partial image processing (picture in picture processing, mask processing, and on-screen display processing in the example of FIG. 1) out of all types of executable image processing is set as the second image processing executed on an external processing signal (digital signal) in the conventional-compatible mode.

The video-output I/F unit 68 is configured by using a DAC (digital to analog converter), encoder, or the like, and it generates video signals for display on the basis of the first imaging signal (digital signal) that has undergone the first image processing in the image processing unit 67 or the external processing signal (digital signal) that has undergone the second image processing in the image processing unit 67. Then, the video-output I/F unit 68 outputs the video signals for display to the display device 5. That is, the video-output I/F unit 68 functions as a video-signal output unit.

The video-input I/F unit 69 is connected to the old processor 7 (a video-output I/F unit 78 described later) through an undepicted connector, cable, or the like, to receive input of external processing signals. Furthermore, the video-input I/F unit 69 outputs external processing signals input from the old processor 7 to the image processing unit 67 (the PinP processing unit 67G in the example of FIG. 1).

Configuration of the Old Processor

The old processor 7 is connectable to only the old scope 3 out of the new and old scopes 2, 3 through the connector 74. Furthermore, the old processor 7 has the same configuration as that of the new processor 6 except that it performs processing on the second imaging signal (analog signal) from the old scope 3 and partial function (the PinP processing unit 67G in the example of FIG. 1) of the image processing unit 67 is omitted. That is, as illustrated in FIG. 1, the old processor 7 includes the control unit 71, a RAM 72, a ROM 73, the connector 74 (the connection detecting unit 74A), an analog processing unit 75, an A/D converter 76, an image processing unit 77 (an OB processing unit 77A, a WB processing unit 77B, an NR processing unit 77C, a γ processing unit 77D, an electronic zoom processing unit 77E, an enhancement processing unit 77F, a mask processing unit 77H, and an OSD processing unit 77I), and the video-output I/F unit 78, which correspond to the control unit 61, the RAM 62, the ROM 63, the connector 64 (the connection detecting unit 64A), the analog processing unit 65, the A/D converter 66, the image processing unit 67 (the OB processing unit 67A, the WB processing unit 67B, the NR processing unit 67C, the γ processing unit 67D, the electronic zoom processing unit 67E, the enhancement processing unit 67F, the mask processing unit 67H, and the OSD processing unit 67I), and the video-output I/F unit 68 in the new processor 6.

Furthermore, according to the present embodiment, the old processor 7 (the control unit 71) communicates with the new processor 6 (the control unit 61) and outputs the signal that corresponds to a detection result (a detection result as to whether the old scope 3 is connected) of the connection detecting unit 74A to the new processor 6 (the control unit 61). Furthermore, when the old scope 3 is connected, the old processor 7 outputs the external processing signal described below to the new processor 6.

Specifically, the analog processing unit 75 and the A/D converter 76 conduct analog processing and A/D conversion on the second imaging signal (analog signal) from the old scope 3. Furthermore, the image processing unit 77 executes all types of executable image processing (in the example of FIG. 1, optical black subtraction processing, white balance adjustment processing, noise reduction processing, gamma processing, electronic zoom processing, edge enhancement processing, mask processing, and on-screen display processing) on the second imaging signal (digital signal) output from the A/D converter 76. Then, the video-output I/F unit 78 generates a video signal for display on the basis of the second imaging signal (digital signal) that has undergone image processing in the image processing unit 77 and outputs the video signal for display as an external processing signal to the new processor 6 (the video-input I/F unit 69).

Here, when the image processing unit 67 (the new processor 6) and the image processing unit 77 (the old processor 7) are compared, with regard to at least any image processing out of the corresponding image processing (optical black subtraction processing, white balance adjustment processing, noise reduction processing, gamma processing, electronic zoom processing, edge enhancement processing, mask processing, and on-screen display processing in the example of FIG. 1), at least any algorithm and parameter of processing are sometimes different due to a version upgrade from the old processor 7 to the new processor 6 although the purpose of image processing is the same.

Operation of the New Processor

Figure 2:
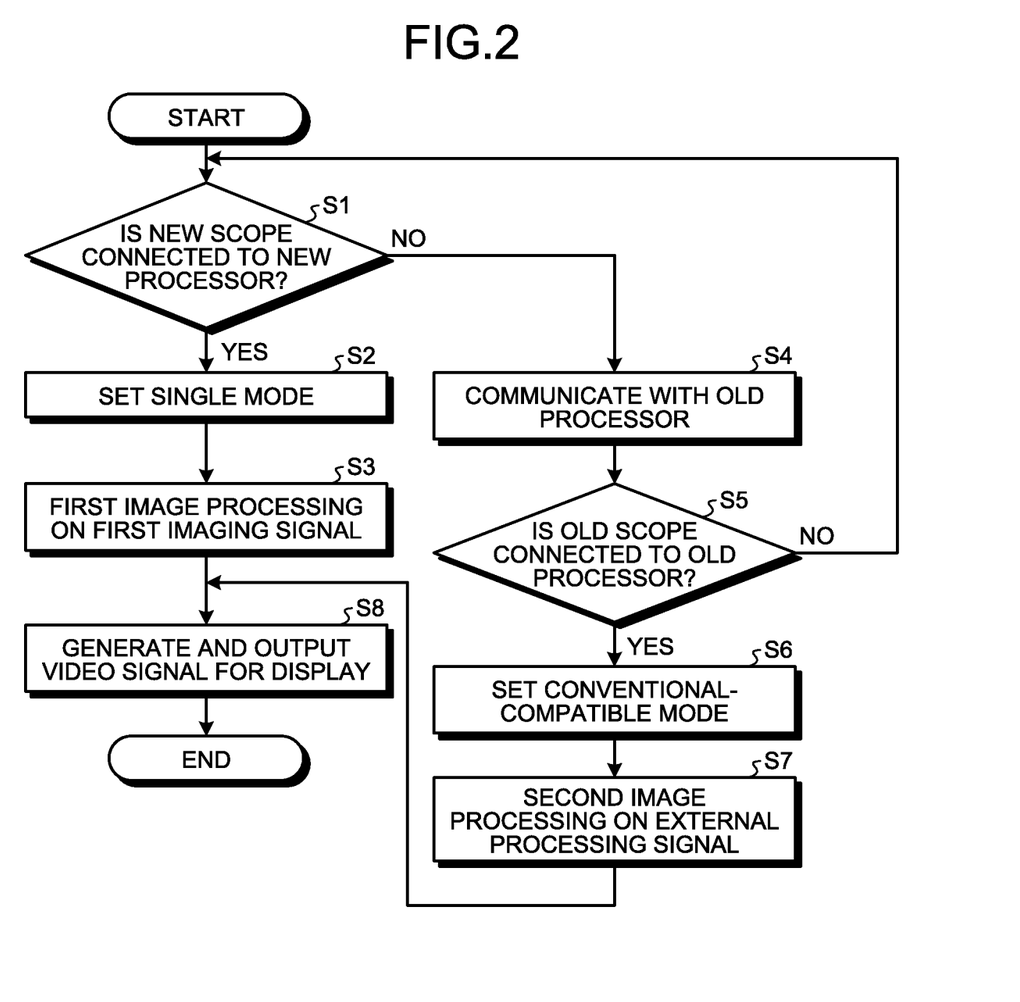
FIG. 2 is a flowchart that illustrates operation of a new processor illustrated in FIG. 1.

FIG. 2 is a flowchart that illustrates operation of the new processor 6.

Next, operation of the above-described new processor 6 (the method for controlling the processor) is explained with reference to FIG. 2.

First, the control unit 61 determines whether the new scope 2 is connected to the new processor 6 in accordance with a detection result of the connection detecting unit 64A (Step S1).

When it is determined that the new scope 2 is connected to the new processor 6 (Step S1: Yes), the control unit 61 sets the single mode as the processing mode of the image processing unit 67 (Step S2: a mode switching step). Then, the image processing unit 67 executes the first image processing on the first imaging signal (digital signal) that has been output from the new scope 2 and has passed through the analog processing unit 65 and the A/D converter 66 under the control of the control unit 61 (Step S3: an image processing step). Then, the new processor 6 proceeds to Step S8.

Conversely, when it is determined that the new scope 2 is not connected to the new processor 6 (Step S1: No), the control unit 61 communicates with the old processor 7 (the control unit 71) (Step S4). Due to the communication, the control unit 61 determines whether the old scope 3 is connected to the old processor 7 (Step S5).

When it is determined that the old scope 3 is not connected to the old processor 7 (Step S5: No), the control unit 61 returns to Step S1.

Conversely, when it is determined that the old scope 3 is connected to the old processor 7 (Step S5: Yes), the control unit 61 sets the conventional-compatible mode as the processing mode of the image processing unit 67 (Step S6: a mode switching step). Then, the image processing unit 67 receives input of an external processing signal from the old processor 7 through the video-output I/F unit 78 and the video-input I/F unit 69 and, under the control of the control unit 61, executes the second image processing on the external processing signal (Step S7: an image processing step). Then, the new processor 6 proceeds to Step S8.

Specifically, in the example of FIG. 1, the image processing unit 67 executes the second image processing described below on an external processing signal from the old processor 7 at Step S7.

Here, the external processing signal is a signal after the image processing unit 77 has conducted all types of executable image processing on the second imaging signal from the old scope 3, as described above. Specifically, the image that corresponds to the external processing signal includes a captured image (in-vivo image) that is captured by the old scope 3 and also a text image such as texts that are attached to an area different from the captured image during on-screen display processing.

Furthermore, at Step S7, after receiving input of an external processing signal, the PinP processing unit 67G conducts picture in picture processing in which the external processing signal is a child image and an image signal for expanding the child image into the entire image area is generated. Next, with respect to the image signal generated by the PinP processing unit 67G, the mask processing unit 67H generates an image signal during processing to mask areas other than the above-described captured image (processing to paint the above-described text image in black). Then, with respect to the image signal generated by the mask processing unit 67H, the OSD processing unit 67I generates an image signal in which the above-described text image such as texts are added again during on-screen display processing.

After Step S3 or S7, the video-output I/F unit 68 generates a video signal for display on the basis of the first imaging signal (digital signal) that has undergone the first image processing or the external processing signal (digital signal) that has undergone the second image processing and outputs it to the display device 5 (Step S8: a video-signal output step).

Through the above-described steps, the display device 5 presents an observation image based on the video signal for display.

The new processor 6 according to the present embodiment described above is capable of switching the processing mode of the image processing unit 67 to the single mode or the conventional-compatible mode. Furthermore, in the single mode, the new processor 6 executes the first image processing on the first imaging signal from the new scope 2. Furthermore, in the conventional-compatible mode, the new processor 6 executes the second image processing on the external processing signal for which the old processor 7 has conducted image processing on the second imaging signal from the old scope 3.

Thus, by setting the conventional-compatible mode as the processing mode of the image processing unit 67, it is possible to comply with the demand of users who desire to use the function provided by only the old processor 7 (e.g., an image processing function to generate images in color that meets preference of a user such as a doctor) while a new function of the new processor 6 is used.

Therefore, there is an advantage such that the new processor 6 according to the present embodiment may improve user-friendliness.

Furthermore, when the old scope 3 is not connected to the old processor 7 and the new scope 2 is connected to the new processor 6, the new processor 6 according to the present embodiment sets the single mode as the processing mode of the image processing unit 67. Furthermore, when the new scope 2 is not connected to the new processor 6 and the old scope 3 is connected to the old processor 7, the new processor 6 sets the conventional-compatible mode as the processing mode of the image processing unit 67.

That is, the processing mode of the image processing unit 67 may be automatically switched in accordance with connection of the new and old scopes 2, 3 to the new and old processors 6, 7. Therefore, users such as doctors are not forced to perform a complicated task (user's operation on the input device 4) to switch the processing mode as compared to for example a case where the configuration is used to switch the processing mode in accordance with a user's operation on the input device 4. Thus, user-friendliness may be further improved.

Furthermore, with the new processor 6 according to the present embodiment, the second image processing includes on-screen display processing. Therefore, for example, when small-sized texts in a text image are attached during on-screen display processing by the old processor 7, the new processor 6 performs on-screen display processing one more time so that the size of the texts may be changed into a size that meets preference of the user. Thus, user-friendliness may be further improved.

Other Embodiments

Although the embodiment for implementing the present disclosure is explained above, the present disclosure does not need to be limited to only the above-described embodiment.

According to the above-described embodiment, the new and old scopes 2, 3, which are scopes different from each other, are used as first and second endoscopes; however, this is not a limitation, and they may be configured as the identical scope and they may be configured to be attachable and detachable from any of the new and old processors 6, 7.

According to the above-described embodiment, the first image processing is all types of image processing executable by the image processing unit 67, and the second image processing is partial image processing out of all types of image processing. That is, the same kinds of image processing are duplicated in the first and the second image processing; however, this is not a limitation, and the first and the second image processing may be entirely different types of image processing.

According to the above-described embodiment, the image processing executable by the image processing units 67, 77 is, for example, optical black subtraction processing, white balance adjustment processing, noise reduction processing, gamma processing, electronic zoom processing, edge enhancement processing, PinP processing, mask processing, and on-screen display processing; however, this is not a limitation, and other types of image processing are applicable. For example, the image processing executable by the image processing units 67, 77 may include demosaicing processing, gain adjustment processing, image processing for observation of special light, and the like.

Furthermore, the configurations of the image processing units 67, 77 may be different. For example, image processing, which is not installed in the new processor 6 (the image processing unit 67), may be installed in the old processor 7 (the image processing unit 77), or new image processing, which is not installed in the old processor 7 (the image processing unit 77), may be installed in the new processor 6 (the image processing unit 67) for the purpose of improvement in image quality, or the like.

According to the above-described embodiment, the second image processing executed on external processing signals by the image processing unit 67 in the conventional-compatible mode is, for example, PinP processing, mask processing, and on-screen display processing; however, this is not a limitation, and other types of image processing are applicable.

Figure 3:
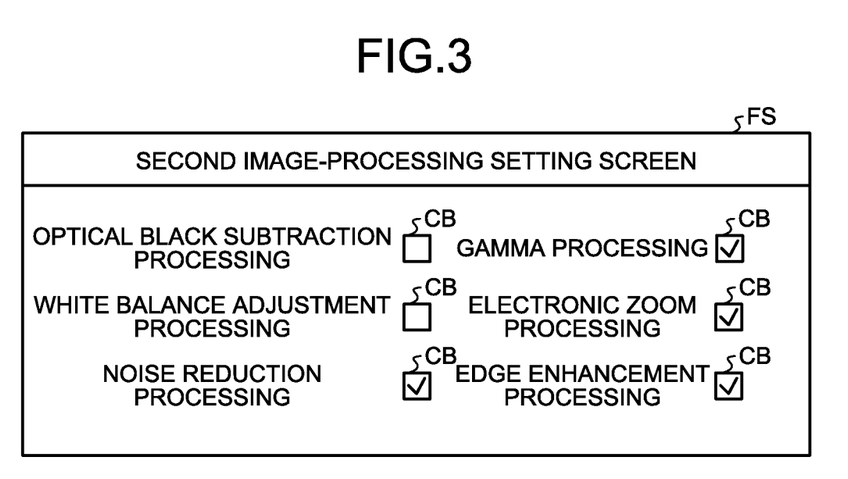
FIG. 3 is a diagram that illustrates a modification of the embodiment.

FIG. 3 is a diagram that illustrates a modification of the embodiment.

For example, the new processor 6 (the control unit 61) causes the display device 5 to present a second image-processing setting screen FS illustrated in FIG. 3 in accordance with a user's operation on the input device 4. Then, the control unit 61 sets, as the second image processing, image processing (noise reduction processing, gamma processing, electronic zoom processing, and edge enhancement processing are selected in the example of FIG. 3) that are selected (selected in check boxes CB in the example of FIG. 3) in accordance with user's operation on the input device 4 in addition to PinP processing, mask processing, and on-screen display processing.

With this configuration, simple user's operation allows the image processing unit 67 to conduct the second image processing that meets preference of a user, such as doctor. Thus, user-friendliness may be further improved.

According to the above-described embodiment, the old processor 7 conducts analog processing and A/D conversion on the second imaging signal (analog signal) output from the old scope 3 and also conducts all types of image processing executable by the image processing unit 77. Furthermore, the old processor 7 outputs, as an external processing signal, a video signal for display generated on the basis of the second imaging signal (digital signal) after the image processing to the new processor 6; however, this is not a limitation.

Figure 4:
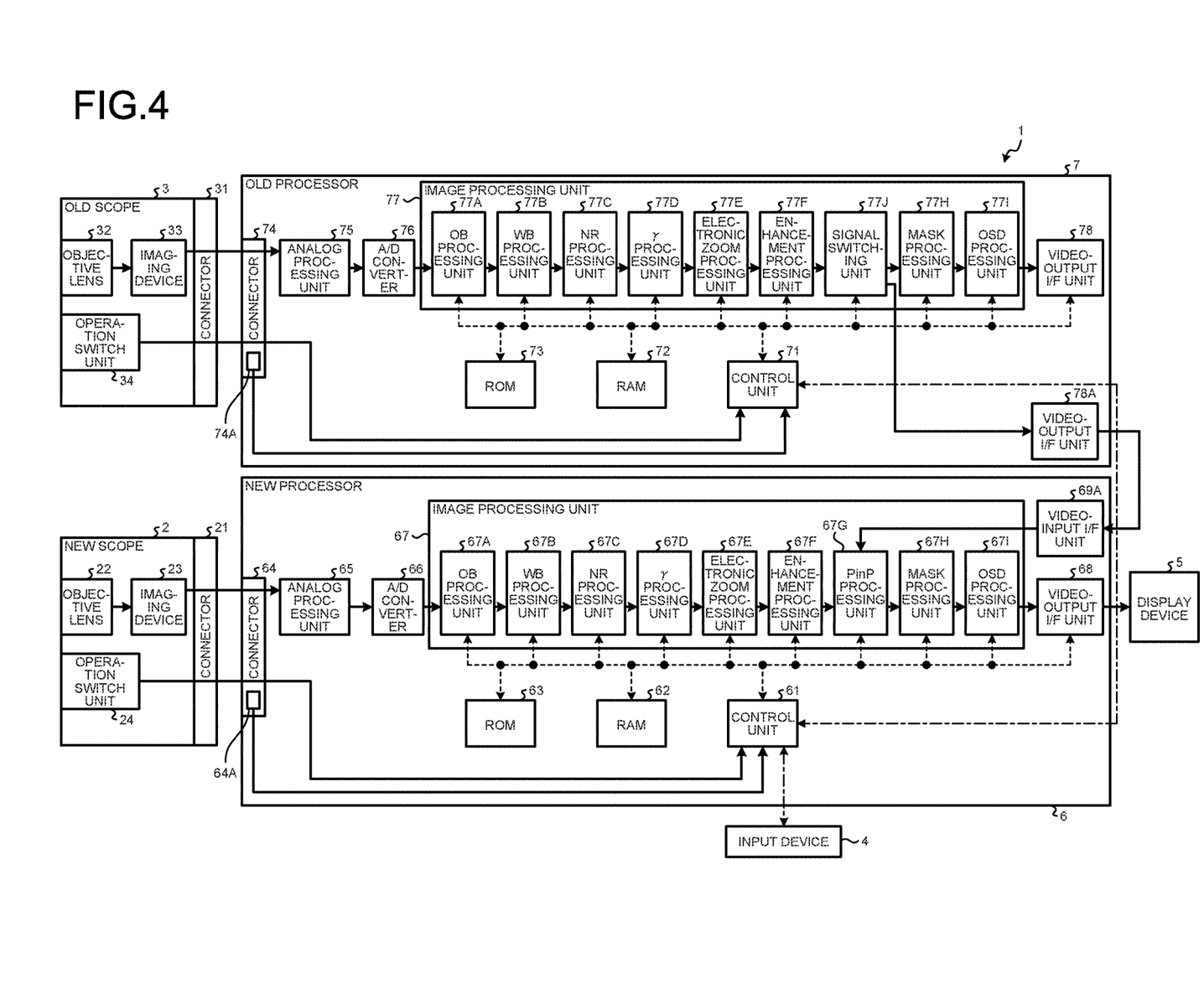
FIG. 4 is a diagram that illustrates a modification of the embodiment.

FIG. 4 is a diagram that illustrates a modification of the embodiment.

As illustrated in FIG. 4, the new processor 6 is provided with a video-input I/F unit 69A that is connected to the old processor 7 (a video-output I/F unit 78A described later) through an undepicted connector, cable, or the like, to receive input of external processing signals instead of the video-input I/F unit 69 that is explained in the above-described embodiment. The video-input I/F unit 69A outputs received external processing signals to the image processing unit 67 (the PinP processing unit 67G in the example of FIG. 4).

Furthermore, as illustrated in FIG. 4, the video-output I/F unit 78A that corresponds to the video-input I/F unit 69A is added to the old processor 7. Furthermore, a signal switching unit 77J for switching the output destination of a received signal under the control of the control unit 71 is added to the image processing unit 77.

Furthermore, when the conventional-compatible mode is set, the new processor 6 (the control unit 61) notifies the old processor 7 (the control unit 71) that the conventional-compatible mode is set through communication. The control unit 71 causes the image processing unit 77 to conduct only partial image processing (in the example of FIG. 4, optical black subtraction processing, white balance adjustment processing, noise reduction processing, gamma processing, electronic zoom processing, and edge enhancement processing) out of all types of executable image processing. Furthermore, under the control of the control unit 71, the signal switching unit 77J outputs the second imaging signal (digital signal) that has undergone the partial image processing to the video-output I/F unit 78A. Then, the video-output I/F unit 78A outputs the second imaging signal (digital signal) that has undergone the partial image processing as an external processing signal to the new processor 6 (the image processing unit 67 (the PinP processing unit 67G in the example of FIG. 4) through the video-input I/F unit 69A).

According to the above-described embodiment, in the single mode, all types of executable image processing are conducted on the first imaging signal by the image processing unit 67; however, this is not a limitation.

Figure 5:
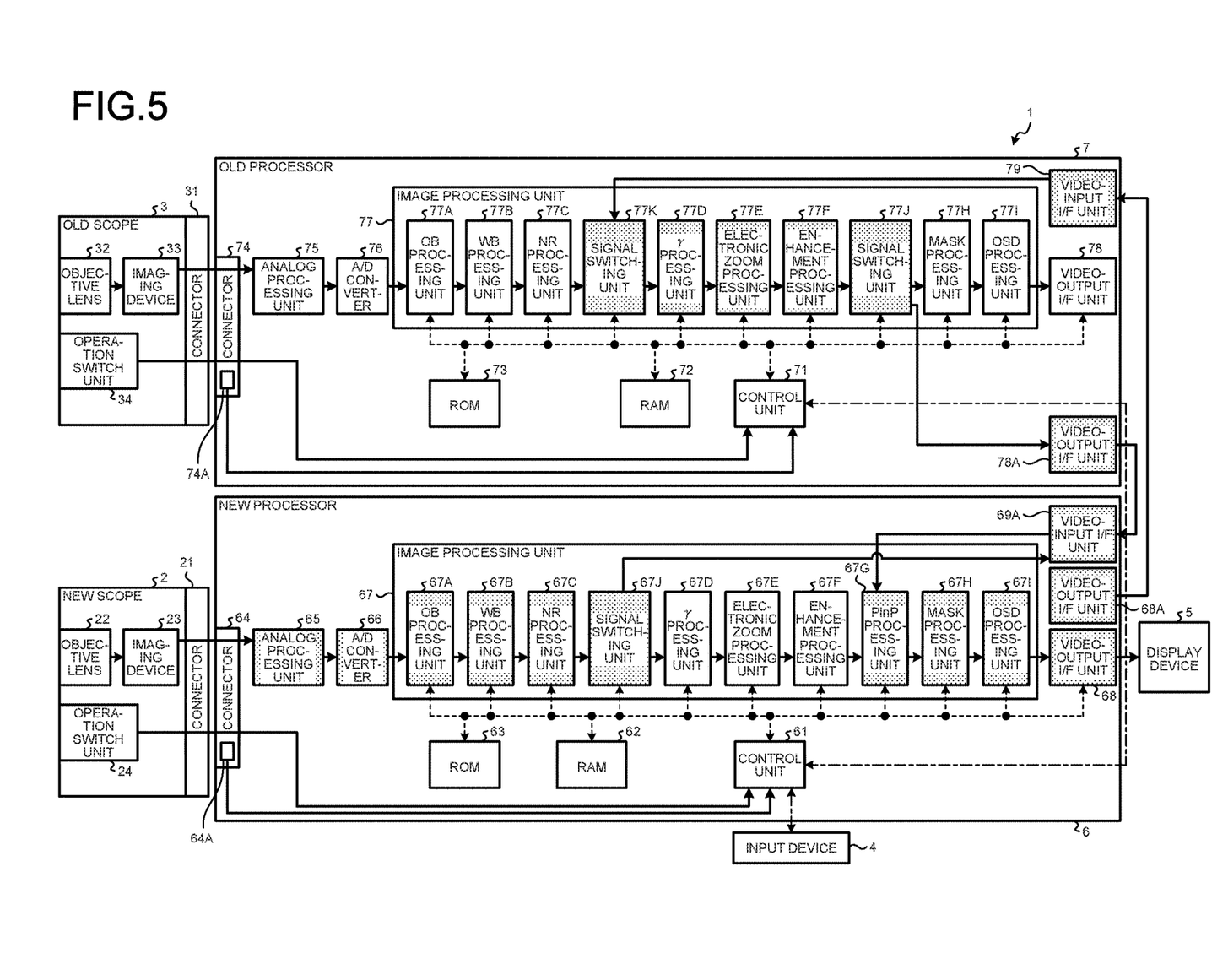
FIG. 5 is a diagram that illustrates a modification of the embodiment.

FIG. 5 is a diagram that illustrates a modification of the embodiment. Here, in FIG. 5, for the convenience of explanation, the block (each of the blocks 65, 66, 67A to 67C, 67G to 67J, 68, 68A, 69A, 77D to 77F, 77J, 77K, 78A, and 79 in the example of FIG. 5) that is in operation in the new and old processors 6, 7 is indicated with a dot pattern.

As illustrated in FIG. 5, a video-output I/F unit 68A is added to the new processor 6 as compared to the configuration illustrated in FIG. 4. Furthermore, a signal switching unit 67J for switching the output destination of an input signal is added to the image processing unit 67.

Furthermore, as illustrated in FIG. 5, as compared to the configuration illustrated in FIG. 4, the old processor 7 has added a video-input I/F unit 79 that corresponds to the video-output I/F unit 68A and that is connected to the video-output I/F unit 68A through an undepicted connector, cable, or the like, to receive signals. The video-input I/F unit 79 outputs received signals to the image processing unit 77. Furthermore, the image processing unit 77 is provided with a signal switching unit 77K that selects and outputs one of signals in two lines under the control of the control unit 71, as compared with the configuration illustrated in FIG. 4.

Furthermore, when the single mode is set, the new processor 6 (the control unit 61) notifies the old processor 7 (the control unit 71) that the single mode is set through communication. Furthermore, the control unit 61 causes the image processing unit 67 to execute only partial image processing (optical black subtraction processing, white balance adjustment processing, and noise reduction processing in the example of FIG. 5) out of all types of executable image processing on the first imaging signal (digital signal) that is output from the new scope 2 and passes through the analog processing unit 65 and the A/D converter 66. Furthermore, under the control of the control unit 61, the signal switching unit 67J outputs the first imaging signal (digital signal) that has undergone the partial image processing to the video-output I/F unit 68A. Then, the video-output I/F unit 68A outputs the first imaging signal (digital signal) that has undergone the partial image processing to the old processor 7 (the image processing unit 77 through the video-input I/F unit 79). Moreover, under the control of the control unit 71, the signal switching unit 77K selects and outputs the first imaging signal (digital signal) output from the video-input I/F unit 79 out of signals in two lines (signals in two lines, i.e., a signal output from the NR processing unit 77C and a signal output from the video-input I/F unit 79 in the example of FIG. 5). Furthermore, under the control of the control unit 71, the image processing unit 77 (the old processor 7) executes only partial image processing (gamma processing, electronic zoom processing, and edge enhancement processing in the example of FIG. 5) out of all types of executable image processing on the first imaging signal (digital signal) output from the signal switching unit 77K. Furthermore, under the control of the control unit 71, the signal switching unit 77J outputs the first imaging signal (digital signal) that has undergone the partial image processing to the video-output I/F unit 78A. Then, the video-output I/F unit 78A outputs the first imaging signal (digital signal) that has undergone the partial image processing to the new processor 6 (the image processing unit 67 through the video-input I/F unit 69A). Furthermore, under the control of the control unit 61, the image processing unit 67 (the new processor 6) executes only partial image processing (picture in picture processing, mask processing, and on-screen display processing in the example of FIG. 5) out of all types of executable image processing on the first imaging signal (digital signal) output from the video-input I/F unit 69A. Then, the video-output I/F unit 68 generates video signals for display on the basis of the first imaging signal (digital signal) that has undergone the partial image processing and outputs them to the display device 5.

According to the above-described embodiment, the new and old scopes 2, 3 are configured as flexible endoscopes; however, this is not a limitation, and they may be configured as, for example, rigid endoscopes.

Furthermore, the process flow is not limited to the steps of the process in the flowchart (FIG. 2) explained in the above-described embodiment, and it may be changed to a degree that there is no contradiction.

Furthermore, the algorithm of the process explained by using the flowchart in this specification may be written as a program. The program may be recorded in a storage unit inside the computer, or it may be recorded on a recording medium readable by the computer. Programs may be recorded in a storage unit or a recording medium when the computer or the recording medium is shipped as a product, or it may be recorded by being downloaded via a communication network.

With the processor, the endoscope system, the method for controlling the processor, and the control program, there is an advantage such that user-friendliness is improved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
a first processor comprising hardware, the first processor being configured to process a first imaging signal acquired by a first endoscope;
a second processor comprising hardware, the second processor being communicably connected to the first processor and configured to process a second imaging signal acquired by a second endoscope;
a first connector provided in the first processor, the first endoscope being connected to the first processor by the first connector;
a second connector provided in the second processor, the second endoscope being connected to the second processor by the second connector;
wherein the first processor is configured to:
switch a processing mode of image processing to one of a first processing mode and a second processing mode in accordance with a connection state of the first processor to the first endoscope and a connection state of the second processor to the second endoscope;
execute first image processing on the first imaging signal when the processing mode is switched to the first processing mode and to execute second image processing on an signal input from the second processor when the mode switch switches the processing mode is switched to the second processing mode; and
generate a video signal for display based on an output signal from the first processor and output the video signal to an external device.

2. The endoscope system according to claim 1, wherein:
the first connector is configured to detect whether the first endoscope is connected to the first processor; and
the second connector is configured to detect whether the second endoscope is connected to the second processor and to output a detection result to the first processor;
wherein the first processor is configured to receive the detection result from the second processor.

3. The endoscope system according to claim 1, wherein the first processor is configured to receive an operation input from a user, and
the second image processing is image processing designated by the operation input from the user among multiple types of preset image processing.

4. The endoscope system according to claim 1, wherein the first image processing includes multiple types of image processing, and
the second image processing is a part of the types of image processing in the first image processing.

5. The endoscope system according to claim 1, wherein the second image processing includes at least on-screen display processing.

6. The endoscope system according to claim 1, further comprising:
the first endoscope configured to be connected to the first processor and output the first imaging signal to the first processor; and
the second endoscope configured to be connected to the second processor and output the second imaging signal to the second processor.

7. The endoscope system according to claim 1, wherein the first processor is configured to:
switch the processing mode to the first processing mode when the first endoscope is connected to the first processor and the second endoscope is not connected to the second processor, and
switch the processing mode to the second processing mode when the first endoscope is not connected to the first processor and the second endoscope is connected to the second processor.

* * * * *